(12) United States Patent
Struhl et al.

(10) Patent No.: US 6,576,469 B1
(45) Date of Patent: Jun. 10, 2003

(54) INDUCIBLE METHODS FOR REPRESSING GENE FUNCTION

(75) Inventors: Kevin Struhl, Weston, MA (US); Zarmik Moqtaderi, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/508,400

(22) PCT Filed: Sep. 10, 1998

(86) PCT No.: PCT/US98/19026
§ 371 (c)(1),
(2), (4) Date: Sep. 19, 2000

(87) PCT Pub. No.: WO99/13077
PCT Pub. Date: Mar. 18, 1999

Related U.S. Application Data

(60) Provisional application No. 60/058,474, filed on Sep. 10, 1997.

(51) Int. Cl.[7] .......................... C12N 15/63; C12N 15/81
(52) U.S. Cl. ................. 435/483; 435/69.1; 435/254.21; 435/325; 435/455
(58) Field of Search ................. 435/69.1, 325, 435/254.11, 455

(56) References Cited

U.S. PATENT DOCUMENTS

| | | | |
|---|---|---|---|
| 5,093,242 A | * | 3/1992 | Bachmair et al. |
| 6,004,779 A | * | 12/1999 | Bradley et al. |

FOREIGN PATENT DOCUMENTS

| | | |
|---|---|---|
| EP | 0136907 A2 * | 4/1985 |
| WO | WO 88/02406 | 4/1988 |
| WO | WO 89/09829 | 10/1989 |
| WO | WO 94/29442 | 12/1994 |
| WO | WO 95/21267 | 8/1995 |
| WO | WO 96/01313 | 1/1996 |

OTHER PUBLICATIONS

Lundblad et al (1997) in: Current Protocols in Molecular Biology, Ausubel et al, eds. John Wiley and Sons, Inc., pp. 13.10.11–13.10.14.*
Shockett et al (1995) PNAS 92:6522–6526.*
Baker et al (1995) J. Biol. Chem. 270(20): 120–65–12074.*
Winnacker (1987) From Genes to Clones, Introduction to Gene Technology, VCH, Weinheim, New York, pp. 241 and 352.*
Aubrecht et al.; "Controlled Gene Expression in Mammalian Cells Via a Regulatory Cascade Involving the Tetracycline Transactivator and lac Repressor", Gene, 172: 227–231, (1996).
Bartel et al.; "The Recognition Component of the N–end Rule Pathway", The Embo Journal, 9(10): 3179–3189, (1990).
Deuschle et al.; "Tetracycline –Reversible Silencing of Eukaryotic Promoters", Molecular and Cellular Biology, 15(4): 1907–1914 (1995).
Dohmen et al.; "The N–end Rule is Mediated by the UBC2(RAD6) Ubiquitin–Conjugating Enzyme", Proc. Natl. Acad. Sci. USA, 88: 7351–7355 (Aug. 1991).
Gossen et al.; "Inducible Gene Expression Systems for Higher Eukaryotic Cells", Current Opinion in Biotechnology 5: 516–520 (1994).
Moqtaderi et al.; "TBP–associated Factors are not Generally Required for Transcriptional Activation in Yeast", Nature 383: 188–191 (Sep. 12, 1996).
Shockett E. P. and Schatz; "Diverse Strategies for Tetracycline–regulated Inducible Gene Expression", Proc. Natl. Acad. Sci. USA , 93: 5173–5176, (May 1996).

* cited by examiner

Primary Examiner—Remy Yucel
Assistant Examiner—Bronwen M. Loeb
(74) Attorney, Agent, or Firm—Foley Hoag LLP

(57) ABSTRACT

Methods for the rapid repression of gene function in eucaryotic cells are disclosed including inducible means for both shutting down a targeted gene's transcription and rapidly removing a targeted gene's polypeptide product.

47 Claims, 3 Drawing Sheets

INDUCIBLE METHODS FOR REPRESSING GENE FUNCTION

REFERENCE TO CROSS-RELATED APPLICATIONS

Figure 1A:
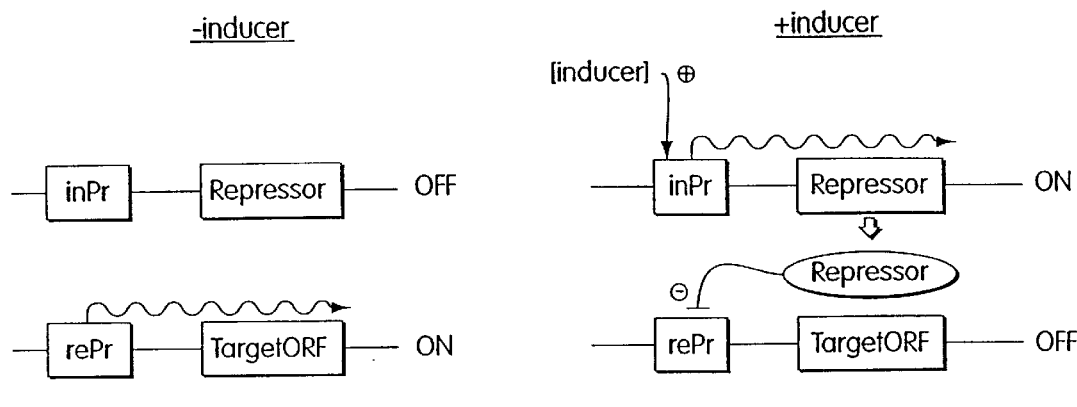

This application is the National Stage of International Application No. PCT/US98/19026, filed on Sep. 10, 1998, which claims the benefit of U.S. Provisional Application No. 60/058,474, filed Sep. 10, 1997, the contents of both of which are specifically incorporated by reference herein.

STATEMENT OF RIGHTS

This invention was made during the course of work supported by the National Institutes Health grant No. GM30186. The U.S. Government has certain rights in the invention.

1. BACKGROUND OF THE INVENTION

Genetics is essentially an approach to understanding biological processes through the systematic elimination of gene function. Historically, the genetic approach has involved the development of "screens" for mutations in genes which affect a specific phenotypic trait of an organism. The great advantage of this approach has been that no prior knowledge of the molecular nature of the genes involved is required because the "screen" identifies the affected genes by marking them with mutations. The mutation involved is frequently a change in the gene's sequence which results in a loss-of-function of the encoded gene product. Unfortunately the genetic approach has many limitations. Indeed the study of essential genes, required for cell viability, is exceedingly difficult using a purely genetic approach. As the famous molecular biologist David Botstein once put it, "death is not a phenotype;" an expression which encapsulates the frustration of attempting to study the function of essential genes. The implementation of "reverse genetics" in yeast (see e.g. Winston et al. (1983) Methods Enzymol 101: 211–28) and, later, in mammals (see e.g. Capecchi (1989) Science 244: 1288–92), has allowed the positive identification of a gene as essential through the inability to recover viable yeast haploid gene "knockout" spores or homozygous recessive "knockout" mice. Nevertheless, the exact biological processes in which the essential gene is involved are difficult to determine due to the inability to isolate and/or study the doomed knockout yeast spore or the inviable homozygous mouse zygote. Thus the downstream effects on specific aspects of cell function following removal of the essential gene product cannot be readily determined using these traditional "knockout" studies. Furthermore, while traditional gene "knockout" experiments may be useful in demonstrating that a given gene is essential for the life of the organism, they provide no data on precisely how important the gene is or to what extent so-called "second-site suppressing" mutations can arise which restore cell viability following the removal of the essential gene. These considerations are important in the selection of targets for the rational design of, for example, antibiotic or chemotherapeutic pharmaceutical agents.

Others have endeavored to devise systems for the directed inactivation of a specific target gene in a host eucaryotic cell. For example, in an attempt to provide for a systematic means of deriving temperature-sensitive conditional alleles of a given gene target, Dohmen et al. have devised a temperature-sensitive "degron" cassette that can be appended to any gene of interest and used to render it thermosensitive (Dohmen et al. (1994) Science 263: 1273–6). This approach could thus be applied in theory to any essential gene of interest. However, the generality with which the thermosensitive degron can be successfully applied to specific gene targets has yet to be determined and the necessity of relying upon thermal induction for the resulting system is a major drawback. Indeed, eucaryotic cells experience a transient heat-shock response which can have profound effects on some cellular processes such as transcription. Furthermore, the requirement for induction by heat shock precludes useful application to mammalian transgenic animal systems. Still other systems have been developed for the specific targeted removal of a host gene. Notably the Cre/lox system (see e.g. Sauer (1998) Mehods 14: 381–92) allows for the inducible deletion of a specific target gene through the action of the Cre site-specific DNA recombinase. Using this system, genetic switches can be designed to target ablation of a target gene in a specific tissue and at a specific time during development. One shortcoming of this method is that, following recombinational deletion of the targeted gene from the chromosome, the remaining mRNA and polypeptide products of the gene may only slowly be titrated out of the host cell through consecutive mitotic cell divisions and/or the eventual turnover of the mRNA and polypeptide by cellular ribonucleases and proteases. Thus it would be desirable to have a more rapid means for directly inactivating specific target genes in a host eucaryotic cell.

2. SUMMARY OF THE INVENTION

In general, the present invention provides a rapid and effective means for inactivating target genes, including target genes involved in important biological pathways. The invention also provides a system for the rapid and reliable repression of gene function regardless of whether the gene of interest is known or suspected of being an essential gene.

In one aspect, the present invention provides multiple means for the rapid and inducible elimination of gene function in a controlled and reproducible manner in a population of otherwise mitotically viable eucaryotic cell. The methods described include a method for rapidly repressing the transcription of a target gene through the action of an inducible repressor, a method for rapidly removing the polypeptide product of a target gene through directed proteolysis, and an integrated method in which both transcriptional repression and directed proteolysis occurs. In one embodiment, the method provides an inducible means for the passive removal of an mRNA product of a target gene (i.e. new target gene mRNA synthesis is blocked and the existing target gene mRNA is allowed to degrade through the natural turnover of the remaining target mRNA). In another embodiment, the method provides an inducible means for the active removal of a polypeptide product of a target gene (i.e. while new target gene polypeptide synthesis, or translation, is not blocked per se, the existing target gene polypeptide product is actively degraded by proteolysis). In yet another, preferred embodiment, the first and second embodiments are "integrated" thereby allowing an optimal rate at which gene function can be eliminated by the simultaneous removal of both mRNA and polypeptide products of the gene.

The present invention thus provides a method of determining which genes represent effective targets for the design of antibiotic and/or chemotherapeutic agents. In particular, an array of essential genes can be screened to determine which are most vital to cell viability using the method of the invention. For example, essential genes which, when targeted for destruction by this two-pronged inducible repression system, result in the immediate death of the host cell, are likely to be effective targets for antibiotic or chemotherapeutic agents designed to stop cell growth. The present invention further provides a means of genetically modifying a population of cells so as to render them subject to killing by a normally benign inducing agent. This modification provides a convenient way to terminate or attenuate the physiological effects on a host organism of a population of bioengineered cells which have been delivered to the host. In this application, virtually any essential gene can be targeted for the inducible repressional shut-off of the present invention. In still other applications, a bioengineered cell population which produces a specific physiologically active gene product could be designed so that the gene product itself is subject to the inducible repressional shut-off system. When such a bioengineered cell population is introduced into a host, the delivery of the physiologically active gene product produced by the bioengineered cells can be adjusted throughout the lifetime of the host/cell combination by administration of a benign inducing agent.

3. BRIEF DESCRIPTION OF THE FIGURES

Figure 1B:
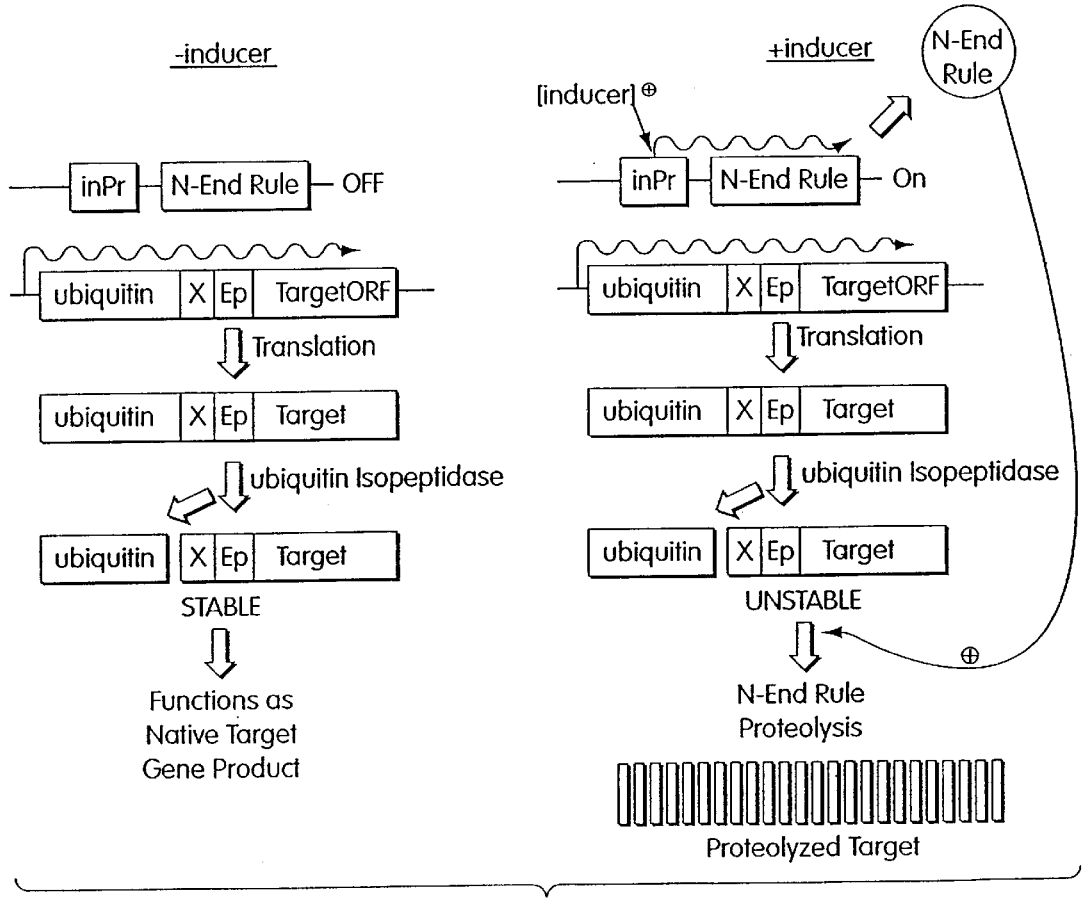

FIGS. 1A and B provide a generalized illustration of the essential components of the method for inducible repression of a target gene. The two prongs of the method are illustrated separately here for clarity. FIG. 1A diagrams the essential elements of the first prong of the method—the inducible transcriptional shut-off of a target gene. FIG. 1B diagrams the essential elements of the second prong of the method—the inducible degradation of the target polypeptide.

Figure 2A:
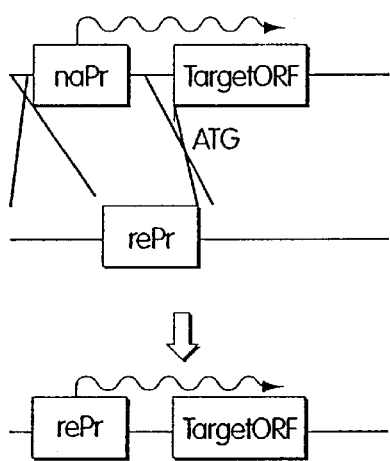
Figure 2B:
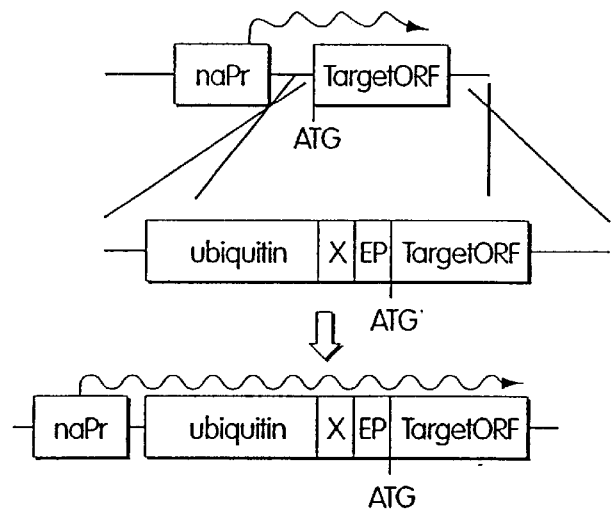

FIG. 2 illustrates the manner in which a target gene is modified to become newly susceptible to the two prongs of the repression method. FIG. 2A illustrates the replacement of a native target gene promoter (naPr) with a repressible promoter (rePr) which is responsive to an inducible repressor. FIG. 2A thus illustrates the modifications essential to make the target gene susceptible to the inducible transcriptional shut-off prong. FIG. 2B illustrates the insertion of a ubiquitin coding sequence (Ub) and a unique codon (X), destined to become the amino-terminal amino acid residue of the target polypeptide, upstream of the target polypeptide-encoding sequence, or target "ORF." An optional epitope tag (Ep) marker for the target gene is also indicated in the figure. FIG. 2B thus illustrates the modifications essential to make the target gene susceptible to the inducible N-end rule proteolytic effector.

Figure 3:
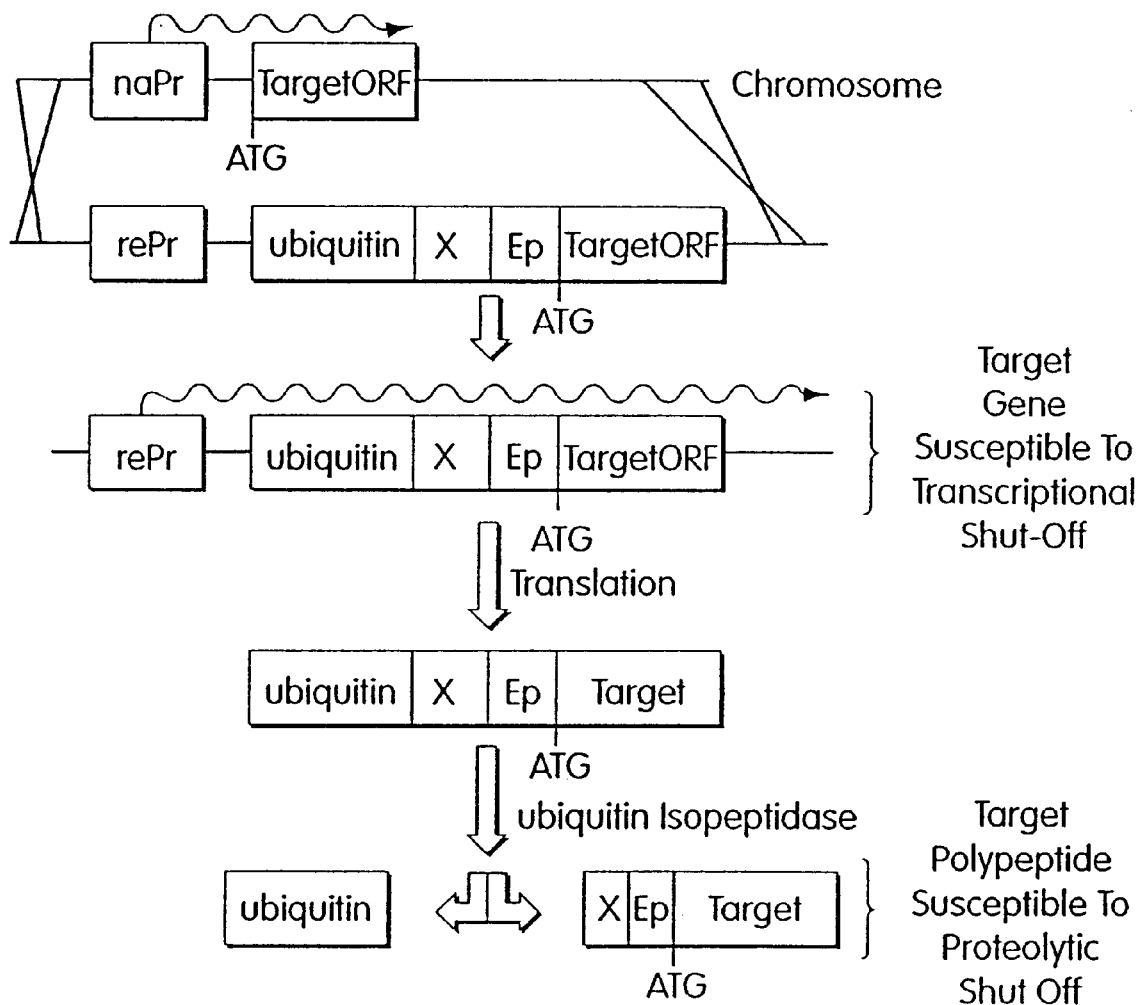

FIG. 3 illustrates the generalized structure of a target gene which has been modified so as to be made susceptible to the action of both the transcriptional shut-off prong and the directed proteolysis prong of the method. This preferred embodiment of the modified target gene can be readily transplaced into the eucaryotic genome at the site of the native target gene by standard "knock-in" technology as shown in the figure.

4. DETAILED DESCRIPTION OF THE INVENTION

4.1 General

The two prongs of the method are illustrated separately in FIG. 1 for clarity, but it is understood that, in a preferred embodiment, the two prongs are employed simultaneously to maximize the speed and efficacy of the method. Panel A diagrams the essential elements of the first prong of the method—the inducible transcriptional shut-off of a target gene. Panel B diagrams the essential elements of the second prong of the method—the inducible degradation of the target polypeptide. Both prongs rely on the use of an inducible promoter (inPr) to drive the inducible expression of an effector of suppression. In Panel A, the effector of suppression is a transcriptional repressor which is capable of repressing transcription from a repressible promoter (rePr). In panel B, the effector of suppression is a component of the N-end rule pathway which effects the proteolytic destruction of polypeptides possessing certain amino-terminal amino acid residues. Both prongs further rely on the construction of a synthetic version of the target gene which has been engineered from its native form so as to be uniquely sensitized to the effectors of suppression described above. As shown in FIG. 2A, the target gene can be modified so that its native promoter is replaced by a natural or synthetic promoter (rePr) which is subject to repression by the inducible repressor. This alteration of the target gene potentiates repression by the transcriptional shut-off prong of the method. As shown in FIG. 2B, the target gene can also be modified so that its encoded polypeptide (the target ORF—target open reading frame) is fused in frame to the carboxy-terminal codon of a ubiquitin-encoding sequence. Furthermore a unique amino-terminal amino acid encoding codon is engineered at the point of fusion of the two coding sequences—i.e. just downstream of ubiquitin's final glycine codon and just before the target ORF.

4.2 Definitions

The term "agonist", as used herein, is meant to refer to an agent that mimics or upregulates (e.g. potentiates or supplements) bioactivity of the protein of interest. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide of interest with another molecule, e.g, a target peptide or nucleic acid.

"Antagonist" as used herein is meant to refer to an agent that downregulates (e.g. suppresses or inhibits) bioactivity of the protein of interest. An antagonist can be a compound which inhibits or decreases the interaction between a protein and another molecule, e.g., a target peptide, such as interaction between ubiquitin and its substrate. An antagonist can also be a compound that downregulates expression of the gene of interest or which reduces the amount of the wild type protein present.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "cell death" or "necrosis", is a phenomenon when cells die as a result of being killed by a toxic material, or other extrinsically imposed loss of function of a particular essential gene function.

"Biological activity" or "bioactivity" or "activity" or "biological function", which are used interchangeably, for the purposes herein means a catalytic, effector, antigenic or molecular tagging function that is directly or indirectly performed by the polypeptides of this invention (whether in its native or denatured conformation), or by any subsequence thereof.

As used herein the term "bioactive fragment of a polypeptide" refers to a fragment of a full-length polypeptide, wherein the fragment specifically agonizes (mimics) or antagonizes (inhibits) the activity of a wild-type polypeptide. The bioactive fragment preferably is a fragment capable of interacting with at least one other molecule, protein or DNA, with which a full length protein can bind.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g. polypeptide portion) foreign to and not substantially homologous with any domain of a polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The terms "epitope" and "epitope tag", as used herein, are meant to refer to any of various convenient molecular markers known in the art, such as hemagluttinin or FLAG, so that the level of a polypeptide can be confirmed in a Western blot using, for example, a suitable anti-flu or anti-FLAG antibody.

The term "equivalent" is understood to include nucleotide sequences encoding functionally equivalent polypeptides of or functionally equivalent peptides having an activity of a protein such as described herein. Equivalent nucleotide sequences will include sequences that differ by one or more nucleotide substitutions, additions or deletions, such as allelic variants; and will, therefore, include sequences that differ from the nucleotide sequence of a gene, due to the degeneracy of the genetic code.

As used herein, the terms "gene", "recombinant gene" and "gene construct" refer to a nucleic acid comprising an open reading frame encoding a polypeptide of the present invention, including both exon and (optionally) intron sequences.

A "recombinant gene" refers to nucleic acid encoding a polypeptide and comprising-encoding exon sequences, though it may optionally include intron sequences which are derived from, for example, a chromosomal gene or from an unrelated chromosomal gene. The term "intron" refers to a DNA sequence present in a given gene which is not translated into protein and is generally found between exons.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the—sequences of the present invention.

The term "interact" as used herein is meant to include detectable interactions (e.g. biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant gene is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a—polypeptide is inserted into a suitable expression vector which is in turn used to transform a host cell to produce the heterologous protein. Moreover, the phrase "derived from", with respect to a recombinant—gene, is meant to include within the meaning of "recombinant protein" those proteins having an amino acid sequence of a native—polypeptide, or an amino acid sequence similar thereto which is generated by mutations including substitutions and deletions (including truncation) of a naturally occurring form of the polypeptide.

The term "repression" as used herein is meant to include "inducible repression" and is used to refer to transcriptional repression as by a transcriptional repressor such as a DNA binding transcriptional repressor which binds a target promoter (a "repressible" promoter) to be repressed.

The term "degrading" as used herein is meant to include "inducible degradation" and is used to refer to proteolytic degradation as may be facilitated by a component of the N-end rule proteolytic pathway. Such an "inducible degradation," as referred to herein, is meant to describe the targeted degradation of a specific "target gene polypeptide."

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

"Transcription" is a generic term used throughout the specification to refer to DNA sequences, such as initiation signals, enhancers, and promoters, which induce or control transcription of protein coding sequences with which they are operably linked. "Transcriptional repressor," as used herein, refers to any of various polypeptides of procaryotic, eucaryotic origin, or which are synthetic artificial chimeric constructs, capable of repression either alone or in conjunction with other polypeptides and which repress transcription in either an active or a passive manner as described elsewhere. It will also be understood that the recombinant gene can be under the control of transcriptional regulatory sequences which are the same or which are different from those sequences which control transcription of the naturally-occurring forms of—polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the polypeptide is disrupted.

As used herein, the term "target gene" refers to the nucleic acid which encodes a gene of interest. The target gene can be an "essential" gene, required for continued cell viability whose function is to be shut-off by the method of the invention. The term "target gene" is used to refer to both the original gene to be targeted for shut-off and the same gene as later modified for shut-off (such as by the replacement of the native promoter with a repressible promoter and the addition of a ubiquitin-X encoding sequence to the amino terminus of the targeted ORF, or open reading frame). The term "target polypeptide" is used interchangeably with the term "target gene polypeptide" and refers to the polypeptide gene product of the target gene as described above.

As used herein, the term "transgene" means a nucleic acid sequence (encoding, e.g., one of the polypeptides, or an antisense transcript thereto) which has been introduced into a cell. A transgene could be partly or entirely heterologous, i.e., foreign, to the transgenic animal or cell into which it is introduced, or, homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the polypeptide, e.g. either agonistic or antagonistic forms. However, transgenic animals in which the recombinant—gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "ubiquitin" as used herein refers to an abundant 76 amino acid residue polypeptide that is found in all eukaryotic cells. The ubiquitin polypeptide is characterized by a carboxy-terminal glycine residue that is activated by ATP to a high-energy thiol-ester intermediate in a reaction catalyzed by a ubiquitin-activating enzyme (E1). The activated ubiquitin is transferred to a substrate polypeptide via an isopeptide bond between the activated carboxy-terminus of ubiquitin and the epsilon-amino group of a lysine residue (s) in the protein substrate. This transfer requires the action of ubiquitin conjugating enzymes such as E2 and, in some instances, E3 activities. The ubiquitin modified substrate is thereby altered in biological function, and, in some instances, becomes a substrate for components of the ubiquitin-dependent proteolytic machinery which includes both ubiquitin isopeptidase enzymes as well as proteolytic proteins which are subunits of the proteasome. As used herein, the term "ubiquitin" includes within its scope all known as well as unidentified eukaryotic ubiquitin homologs of vertebrate or invertebrate origin. Examples of ubiquitin polypeptides as referred to herein include the human ubiquitin polypeptide which is encoded by the human ubiquitin encoding nucleic acid sequence (GenBank Accession Numbers: U49869, X04803) as well as all equivalents. Equivalent ubiquitin polypeptide encoding nucleotide sequences are understood to include those sequences that differ by one or more nucleotide substitutions, additions or deletions, such as allelic variants; as well as sequences which differ from the nucleotide sequence encoding the human ubiquitin coding sequence, due to the degeneracy of the genetic code. Another example of a ubiquitin polypeptide as referred to herein is murine ubiquitin which is encoded by the murine ubiquitin encoding nucleic acid sequence (GenBank Accession Number: X51730).

The term "ubiquitin mutants" as used herein refers to naturally occurring and synthetically derived altered forms of the ubiquitin polypeptide molecule described above. Such mutants include polypeptides encoded by ubiquitin nucleic acid coding sequences containing missense mutations, which produce altered amino acid sequences at a specific residue(s), and nonsense mutations which produce STOP codons resulting in the formation of truncated polypeptide. These mutations also include insertions and deletions which produce frame-shifts or amino acid residue insertions and deletions. These mutants thus produce altered coding sequences resulting in the synthesis of altered forms of the ubiquitin polypeptide other than those described by the term "ubiquitin" as defined above. Examples of ubiquitin mutants described herein include the Ub-75 polypeptide and Ub(K48R). In the Ub-75 polypeptide, the carboxy-terminal glycine codon of ubiquitin is replaced by a stop codon resulting in the synthesis of a mutant ubiquitin polypeptide characterized by a carboxy-terminal glycine residue corresponding to the penultimate glycine residue of wild type ubiquitin. Ub(K48R) is a mutant in which the $48^{th}$ residue of wild type ubiquitin, which corresponds to a lysine residue used in a polyubiquitination cross-linking reaction, is changed to an arginine residue which cannot accommodate the polyubiquitination cross-linking reaction.

The term "ubiquitin-like protein" as used herein refers to a group of naturally occurring proteins, not otherwise describable as ubiquitin equivalents, but which nonetheless show strong amino acid homology to ubiquitin. As used herein this term includes the polypeptides NEDD8, UBL1, NPVAC, and NPVOC. These "ubiquitin-like proteins" are at least over 40% identical in sequence to the human ubiquitin polypeptide and contain a pair of carboxy-terminal glycine residues which function in the activation and transfer of ubiquitin to target substrates as described supra.

As used herein, the term "ubiquitin-related protein" as used herein refers to a group of naturally occurring proteins, not otherwise describable as ubiquitin equivalents, but which nonetheless show some relatively low degree (<40% identity) of amino acid homology to ubiquitin. These "ubiquitin-related" proteins include human Ubiquitin Cross-Reactive Protein (UCRP, 36% identical to huUb, Accession No. P05161), FUBI (36% identical to huUb, GenBank Accession No. AA449261), and Sentrin/Sumo/Pic1 (20% identical to huUb, GenBank Accession No. U83117). The term "ubiquitin-related protein" as used herein further pertains to polypeptides possessing a carboxy-terminal pair of glycine residues and which function as protein tags through activation of the carboxy-terminal glycine residue and subsequent transfer to a protein substrate.

The term "ubiquitin-homologous protein" as used herein refers to a group of naturally occurring proteins, not otherwise describable as ubiquitin equivalents or ubiquitin-like or ubiquitin-related proteins, which appear functionally distinct from ubiquitin in their ability to act as protein tags, but which nonetheless show some degree of homology to ubiquitin (34–41% identity). These "ubiquitin-homologous proteins" include RAD23A (36% identical to huUb, SWISS-PROT. Accession No. P54725), RAD23B (34% identical to huUb, SWISS-PROT. Accession No. P54727), DSK2 (41% identical to huUb, GenBank Accession No. L40587), and GDX (41% identical to huUb, GenBank Accession No. J03589). The term "ubiquitin-homologous protein" as used herein is further meant to signify a class of ubiquitin homologous polypeptides whose similarity to ubiquitin does not include glycine residues in the carboxy-terminal and penultimate residue positions. Said proteins appear functionally distinct from ubiquitin, as well as ubiquitin-like and ubiquitin-related polypeptides, in that, consistent with their lack of a conserved carboxy-terminal glycine for use in an activation reaction, they have not been demonstrated to serve as tags to other proteins by covalent linkage.

The term "ubiquitin conjugation machinery" as used herein refers to a group of proteins which function in the ATP-dependent activation and transfer of ubiquitin to substrate proteins. The term thus encompasses: E1 enzymes, which transform the carboxy-terminal glycine of ubiquitin into a high energy thiol intermediate by an ATP-dependent reaction; E2 enzymes (the UBC genes), which transform the E1-S~Ubiquitin activated conjugate into an E2-S~Ubiquitin intermediate which acts as a ubiquitin donor to a substrate, another ubiquitin moiety (in a poly-ubiquitination reaction), or an E3; and the E3 enzymes (or ubiquitin ligases) which facilitate the transfer of an activated ubiquitin molecule from an E2 to a substrate molecule or to another ubiquitin moiety as part of a polyubiquitin chain. The term "ubiquitin conjugation machinery", as used herein, is further meant to include all known members of these groups as well as those members which have yet to be discovered or characterized but which are sufficiently related by homology to known ubiquitin conjugation enzymes so as to allow an individual skilled in the art to readily identify it as a member of this group. The term as used herein is meant to include novel ubiquitin activating enzymes which have yet to be discovered as well as those which function in the activation and conjugation of ubiquitin-like or ubiquitin-related polypeptides to their substrates and to poly-ubiquitin-like or poly-ubiquitin-related protein chains.

The term "ubiquitin-dependent proteolytic machinery" as used herein refers to proteolytic enzymes which function in the biochemical pathways of ubiquitin, ubiquitin-like, and ubiquitin-related proteins. Such proteolytic enzymes include the ubiquitin C-terminal hydrolases, which hydrolyze the linkage between the carboxy-terminal glycine residue of ubiquitin and various adducts; ubiquitin isopeptidases, which hyrolyze the glycine76-lysine48 linkage between cross-linked ubiquitin moieties in poly-ubiquitin conjugates; as well as other enzymes which function in the removal of ubiquitin conjugates from ubiquitinated substrates (generally termed "deubiquitinating enzymes"). The aforementioned protease activities function in the removal of ubiquitin units from a ubiquitinated substrate following or during uibiquitin-dependent degradation as well as in certain proofreading functions in which free ubiquitin polypeptides are removed from incorrectly ubiquitinated proteins. The term "ubiquitin-dependent proteolytic machinery" as used herein is also meant to encompass the proteolytic subunits of the proteasome (including human proteasome subunits C2, C3, C5, C8, and C9). The term "ubiquitin-dependent proteolytic machinery" as used herein thus encompasses two classes of proteases: the deubiquitinating enzymes and the proteasome subunits. The protease functions of the proteasome subunits are not known to occur outside the context of the assembled proteasome, however independent functioning of these polypeptides has not been excluded.

The term "ubiquitin system" as referred to herein is meant to describe all of the aforementioned components of the ubiquitin biochemical pathways including ubiquitin, ubiquitin-like proteins, ubiquitin-related proteins, ubiquitin-homologous proteins, ubiquitin conjugation machinery, ubiquitin-dependent proteolytic machinery, or any of the substrates which these ubiquitin system components act upon.

4.3 Essential Components of the Method

The following sections describe in detail various alternative embodiments of each of the elements of the general methods described above. In particular, section 4.3.1 describes in detail one necessary component, an inducible promoter, which is useful for either of the two prongs of the method. Furthermore section 4.3.5 provides a description of the various target genes which can be employed in any of the repression methods. Section 4.3.5 also describes methods for modifying the existing native target gene to make it responsive to either or both prongs of the repression system. Section 4.3.2 describes in detail the transcriptional repressors and corresponding repressible promoters which are essential to the design of the transcriptional repression prong of the method. Sections 4.3.3 and 4.3.4 describe in detail the components essential for the polypeptide degradation prong of the method. In particular, section 4.3.3 describes various embodiments of the N-end rule gene which is inducibly deployed to effect proteolysis of the target polypeptide. Section 4.3.4 describes the ubiquitin and ubiquitin equivalent sequences which are used to produce, through endoproteolytic processing of a ubiquitin-target polypeptide fusion protein, target polypeptides possessing unique (generally non-methionine) amino-terminal amino acids which subject the target polypeptide to N-end rule proteolytic processes.

4.3.1 Inducible Promoters

In both prongs of the method of the present invention, an inducible promoter is employed to drive expression of the "effector of suppression." Thus in the inducible transcriptional repression prong of the method the inducible promoter is used to drive expression of the transcriptional repressor, while in the inducible proteolytic degradation prong of the method the inducible promoter is used to drive expression of the N-end rule gene (see FIGS. 1A and 1B). In a preferred mode of the invention, identical or unique inducible promoters are used to drive the independent or coupled expression of both a transcriptional repressor and an N-end rule gene. The inducible promoters of the present invention are capable of functioning in a eucaryotic host organism. Preferred embodiments include naturally occurring yeast and mammalian inducible promoters as well as synthetic promoters designed to function in a eucaryotic host as described below. The important functional characteristic of the inducible promoters of the present invention is their ultimate inducibility by exposure to an environmental inducing agent. Appropriate environmental inducing agents include exposure to heat, various steroidal compounds, divalent cations (including $Cu^{+2}$ and $Zn^{+2}$), galactose, tetracycline, IPTG (isopropyl β-D thiogalactoside), as well as other naturally occurring and synthetic inducing agents and gratuitous inducers. It is important to note that, in certain modes of the invention, the environmental inducing signal can correspond to the removal of any of the above listed agents which are otherwise continuously supplied in the uninduced state (see the tTA based system described below for example). The inducibility of a eucaryotic promoter can be achieved by either of two mechanisms included in the method of the present invention. Suitable inducible promoters can be dependent upon transcriptional activators which, in turn, are reliant upon an environmental inducing agent. Alternatively the inducible promoters can be repressed by a transcriptional repressor which itself is rendered inactive by an environmental inducing agent. Thus the inducible promoter can be either one which is induced by an environmental agent which positively activates a transcriptional activator, or one which is derepressed by an environmental agent which negatively regulates a transcriptional repressor. We note here that the latter class of inducible promoter systems defines transcriptional repressors and corresponding negative cis regulatory elements which can also find use as the repressors and corresponding repressible promoters of the present invention as described in section 4.3.2.

The inducible promoters of the present invention include those controlled by the action of latent transcriptional activators which are subject to induction by the action of environmental inducing agents. Preferred examples include the copper inducible promoters of the yeast genes CUP1, CRS5, and SOD1 which are subject to copper-dependent activation by the yeast ACE1 transcriptional activator (see e.g. Strain and Culotta (1996) Mol Gen Genet 251: 139–45; Hottiger et al. (1994) Yeast 10: 283–96; Lapinskas et al. (1993) Curr Genet 24: 388–93; and Gralla et al. (1991) Proc. Natl. Acad. Sci. USA 88: 8558–62). Alternatively, the copper inducible promoter of the yeast gene CTT1 (encoding cytosolic catalase T), which operates independently of the ACE1 transcriptional activator (Lapinskas et al. (1993) Curr Genet 24: 388–93), can be utilized. The copper concentrations required for effective induction of these genes are suitably low so as to be tolerated by most cell systems, including yeast and Drosophila cells. Alternatively, other naturally occurring inducible promoters can be used in the present invention including: steroid inducible gene promoters (see e.g. Oligino et al. (1998) Gene Ther. 5: 491–6); galactose inducible promoters from yeast (see e.g. Johnston (1987) Microbiol Rev 51: 458–76; Ruzzi et al. (1987) Mol Cell Biol 7: 991–7); and various heat shock gene promoters. Many eucaryotic transcriptional activators have been shown to function in a broad range of eucaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein which induces mammalian promoters containing GAL4 binding sites (Braselmann et al. (1993) Proc Natl Acad Sci USA 90: 1657–61). These and other inducible promoters responsive to transcriptional activators which are dependent upon specific inducing agents are suitable for use with the present invention.

The inducible promoters of the present invention also include those which are repressed by repressors which are subject to inactivation by the action of environmental inducing agents. Examples include procaryotic repressors which can transcriptionally repress eucaryotic promoters which have been engineered to incorporate appropriate repressor-binding operator sequences. Preferred repressors for use in the present invention are sensitive to inactivation by physiologically benign inducing agent. Thus, where the lac repressor protein is used to control the expression of a eucaryotic promoter which has been engineered to contain a lacO operator sequence, treatment of the host cell with IPTG will cause the dissociation of the lac repressor from the engineered promoter and allow transcription to occur. Similarly, where the tet repressor is used to control the expression of a eucaryotic promoter which has been engineered to contain a tetO operator sequence, treatment of the host cell with IPTG will cause the dissociation of the tet repressor from the engineered promoter and allow transcription to occur.

In a preferred embodiment of the invention, the repressor of the inducible promoter is synthesized as a ubiquitin fusion protein conforming to the formula ubiquitin-X-repressor. This can be achieved using the ubiquitin fusion vector systems designed to confer inducible proteolytic sensitivity to the target gene polypeptide as described below. Thus it will be appreciated by the skilled artisan that a rapid induction of a repressible promoter can be achieved by simultaneously delivering an environmental inducing agent which causes dissociation of the repressor from the repressed inducible promoter, and simultaneously promoting the destruction of that repressor by N-end rule directed proteolysis. Degradation of the repressor prevents rebinding to the operator which can result in decreased inducibility of the repressible promoter—a problem which has been recognized in the art (see Gossen et al. (1993) TIBS 18: 471–5). Furthermore, this aspect of the invention can be utilized independently of the targeted shut-off of a gene, to generally increase the inducibility of a eucaryotic expression system which is subject to repression by a repressor. Thus the present invention further provides improved methods for inducible expression of endogenous or heterologous genes in a eucaryotic cell.

As suggested above, the inducible promoters of the present invention include those which are not naturally occurring promoters but rather synthetically derived inducible promoter systems which may make use of procaryotic transcriptional repressor proteins. The advantage of using prokaryotic repressor proteins in the invention is their specificity to a corresponding bacterial operator binding site, which can be incorporated into the synthetic inducible promoter system. These procaryotic repressor proteins have no natural eucaryotic gene targets and affect only the effector of suppression gene which is put under the transcriptional control of the inducible synthetic promoter. This system thereby avoids undesirable side-effects resulting from unintentional alteration of the expression of nontargeted eucaryotic genes when the inducible promoter is induced. A preferred example of this type of inducible promoter system is the tetracycline-regulated inducible promoter system. Various useful versions of this promoter system have been described (see Shockett and Schatz (1996) Proc. Natl. Acad. Sci. USA 93: 5173–76 for review). As suggested above, these tetracycline-regulated systems generally make use of a strong eucaryotic promoter, such as human cytomegalovirus (CMV) immediate early (IE) promoter/enhancer and a tet resistance operator (tetO) which is bound by the tet repressor protein. In a preferred embodiment, the system involves a modified version of the tet repressor protein called a reverse transactivator (rtTA, or rtTA-nls, which contains a nuclear localization signal) which binds tetO sequences only in the presence of the tet derivatives doxycycline or anhydrotetracycline. Using this system, a synthetic human CMV/IE—tetO—promoter driven construct could be induced by 3 orders of magnitude in 20 hrs by the addition of the tet derivatives (see Gossen et al. (1995) Science 268: 1766–9). Thus this system can be used to make the effector of suppression genes of the present invention inducible in response to the delivery of tetracycline derivatives to the targeted eucaryotic cell. Alternatively, a tet repressor fused to a transcriptional activation domain of VP16 (tTA) can be used to drive expression of the inducible promoter of the present invention. In this instance, transcriptional activation of a synthetic human CMV/IE—tetO—promoter driven construct is achieved by the removal of tetracycline since the tTA activator only binds to the tetO in the absence of tet (see Gossen and Bujard (1992) Proc. Natl. Acad. Sci. USA 89: 5547–51). Other synthetic inducible promoter systems are also available for use in the present invention. For example, a lac repressor-VP16 fusion which exhibits a "reverse" DNA binding phenotype (i.e., analogous to rtTA described above, it only binds the lacO operator sequence in the presence of the inducer IPTG) (see Lambowitz and Belfort (1993) Annu Rev Biochem 62: 587–622). This particular synthetic inducible promoter is approximately 1000-fold inducible in the presence of IPTG. Since neither the tet repressor gene nor the lac repressor gene occurs naturally in a eucaryotic cell, systems involving synthetic inducible promoter constructs such as these rely on the further delivery of an expressible copy of the appropriate procaryotic repressor gene. Suitable expression cassettes for this purpose are readily available for heterologous expression in many different eucaryotic cells including various yeast species and mammalian cells.

The present invention thus allows for considerable flexibility in choosing a suitable inducible promoter and corresponding inducing agent. In some embodiments of the invention, the choice of inducible promoter may be governed by the suitability of the required inducing agent. Factors such as cytotoxicity or indirect effects on nontarget genes may be important to consider in this instance. In other instances the choice may be governed by the properties of the inducible system as a whole. In particular, the ease with which the system can be introduced into the appropriate host cell and the speed and strength with which induction of the system occurs following exposure to an inducing agent.

As mentioned above, the inducible promoters of the present invention are used to drive expression of the effector of suppression genes utilized in each of the two prongs of the method of the present invention (see FIGS. 1A & 1B). These effector of suppression genes include transcriptional repressors (described below) and N-end rule system genes (described in section 4.3.3).

4.3.2 Repressors and Corresponding Repressible Promoters

Although these two elements—the transcriptional repressor and the corresponding repressible promoters are understood to be independently implementable by the method of the invention, the choice of one of these elements governs the selection of the other and so they are discussed together here for the sake of convenience. Nonetheless, in preferred embodiments of the invention the two components are separately and independently engineered into the targeted eucaryotic cell. In particular, a host cell engineered to contain an inducible transcriptional repressor and an inducible N-end rule system component, can be maintained independently for an indefinite period of time prior to the introduction of a target gene construct subject to repression by the transcriptional repressor. Such a host cell can serve as a "master cell line" which carries all of the essential components of the two-pronged shutoff system. In preferred embodiments this "master cell line" comprises both an inducible repressor of the target gene and an inducible N-end rule system component for proteolytic destruction of the target polypeptide. It is understood, however, that in certain instances a "master cell line" carrying only one or the other inducible "effector of suppression" of the two-pronged shutoff system will be desired. For example, a cell-line containing only the transcriptional shut-off prong may be used to determine the normal half-life of a target gene. The complete block to target gene transcription in such a case would allow one to follow the rate of degradation of the target polypeptide (for instance by Western analysis) without having to radioactively label the target as in a "pulse-chase" type experiment. The complete master cell line carrying both inducible effectors of suppression is, however, a preferred embodiment of the invention as it allows the creation of multiple otherwise "isogenic" cell lines which differ only in the specific gene which has been engineered to be subject to the inducible transcriptional/proteolytic shut-off system.

Suitable repressors and repressible promoters for use with the immediate invention include those utilizing procaryotic repressors as discussed above in the description of suitable inducible promoter systems. However, the requirements for suitability of a repressor for use as a repressor of the target gene are fewer than are the requirements for a suitable repressor for use in the inducible promoter system of the invention. In particular, such target gene repressors need not be inactivatable by an inducing agent. Thus, the lacI repressor or the tet repressor could be used in this context without regard to the need to reverse their repression with IPTG or tetracycline (inducing agents). This is because reversal of the transcriptional inactivation of the target gene is not generally desired in the present invention. Thus virtually any site-specific DNA binding protein, which is not otherwise a transcriptional activator and for which a high-affinity binding sequence is known, is suitable for use as a repressor in the present invention. The only requirement is that the high affinity binding sequence be incorporated into the repressible promoter used to express the target gene and that the site-specific DNA binding protein, when bound to this sequence, is capable of repressing the transcription of the target gene. Repression can be achieved by either active or passive processes as is generally understood in the art. For example, the procaryotic lacI and tet repressors are generally believed to be capable of repression in eucaryotes due to a passive ability to block trancription from a eucaryotic promoter to which they are bound (so-called "steric" blocking of the transcription apparatus). In contrast, active repression occurs when a DNA binding protein recruits other cellular proteins involved in transcriptional repression. For example, in *Saccharomyces cerevisiae* the Ssn6-Tup1 corepressor is recruited by a number of different DNA-binding repressor proteins. These include ROX1, a preferred repressor of the present invention, which is described in detail below. Other systems sensitive to Ssn6-Tup1 repression in yeast include the DIT1 and DIT2 genes in yeast which are repressed through a cis sequence called NREDIT (Friesen et al. (1998) Genetics 150: 59–73). Negative regulation by the NREDIT sequence responds to mutations in SIN4 and ROX3. Thus, in the present invention, ROX3 could be used as a repressor and the DIT1 or DIT2 promoter (or minimally an heterologous promoter incorporating the NREDIT element) as the repressible promoter used to drive expression of the target gene. Alternatively, the MIG1 zinc-finger protein, which recruits the Ssn6-Tup1 repressor complex to glucose-repressed promoters (Treitel and Carlson (1995) Proc. Natl. Acad. Sci. USA 92: 3132–6), can be used as the repressor of the present invention in conjunction with a suitable glucose-repressible promoter to drive expression of the target gene. Furthermore, virtually any site specific DNA binding protein can be adapted for use as a repressor in the present invention by fusing the DNA binding polypeptide to a protein domain known to recruit the Ssn6-Tup1 complex. For example, the yeast alpha 2 repressor is known to recruit the Ssn6-Tup1 complex and thus the appropriate alpha 2 coding sequence could be fused to virtually and DNA binding polypeptide in order to derive a suitable repressor protein for use in the present invention.

Many examples of eucaryotic transcriptional repressors which "actively" repress transcription through a specific cis element are known in the art and are of use in the present invention. Surprisingly, even some eucaryotic transcriptional activators can be converted into active repressor complexes when bound with an appropriate corepressor protein. For example, MCM1 functions as an activator in yeast but the MCM1/alpha 2 complex is an active repressor complex capable of repressing a cis-linked promoter (see e.g. Jonson and Herskowitz (1985) Cell 42: 237–47). Similarly, the Drosophila developmental regulator Dorsal is a transcriptional activator which behaves as an active repressor when bound to certain cis regulatory elements such as the zen gene VRE (ventral repression element, see e.g. Pan and Courey (1992) EMBO 11: 1837–42). In these instances either the activator (MCM1 or Dorsal for example) or the corepressor with which it acts (alpha 2 or Groucho (Dubnicoff et al. (1997) Genes Dev 11: 2952–7) is suitable for use in the present invention where a suitable responsive promoter element (such as STE6 operator or a zen VRE) is available to control transcription of the target gene.

In a preferred embodiment, the transcriptional repressor of the present invention is ROX1 and the repressible promoter is selected from the group consisting of: ANB1, HEM13, ERG11 and OLE1. ROX1 is a well-studied a transcriptional repressor of hypoxic genes (Lowry, C. V., Cerdan, M. E., and Zitomer, R. (1990) *Mol. Cell Biol.* 10: pp. 5921–5926; Balasubramanian, B., Lowry, C. V., and Zitomer, R. S. (1993) *Mol. Cell Biol.* 13: pp. 6071–6078). ROX1 binds to specific hypoxic concensus sequences located in the upstream of the upstream region of these genes and represses transcription in conjunction with the general repression complex Tup1-Ssn6 (Deckert et al. (1995) Mol Cell Biol 15: 6109–17). When placed under the control of an ACE1-dependent and copper inducible promoter from the yeast genes CUP1, CRS5, or SOD1, the inPr-ROX1 construct can be stably integrated into the yeast genome, for example, by conventional two-step gene replacement. In the absence of copper, ROX1 is not expressed. However when copper is added to the strain, ROX1 is expressed to levels high enough to repress its target genes, but not high enough to impair cell growth, as occurs with galactose-inducible ROX1 constructs (Deckert, J., Perini, R., Balasubramanian, B., and Zitomer, R. S. (1995) *Genetics* 139: pp. 1149–58).

In preferred embodiments employing the ROX1 repressor, a 5′ fragment of the coding sequence of the target gene of interest can then be genetically modified so that the ROX1-repressible promoter, such as the ANB1 promoter, replaces the native promoter (naPr) of the target gene as shown in FIG. 2A. This genetic modification can be achieved by either standard recombinant DNA subcloning manipulations which are known in the art, or by in vivo homologous cross-over events which occur at a relatively high frequency from double-stranded DNA ends in Saccharomyces cerevisiae and which can also be selected for in mammalian systems using a "double selection" method known in the art. This ANB1 driven allele, when introduced into the inPr-ROX1 parent strain, renders the resulting ANB1 driven allele susceptible to repression by the inducing agent of the inducible promoter. Where the inducible promoter (inPr) is a copper-inducible promoter such as from CUP1, the resulting host cell will express the target gene constitutively in the absence of $Cu^{+2}$. Addition of $Cu^{+2}$ causes the rapid ROX1-dependent transcriptional repression of the target gene. In the absence of de novo synthesis of the target gene mRNA, the existing pool of target gene mRNA will be degraded through normal mRNA "turnover" processes. Thus no further de novo target gene polypeptide synthesis can occur and only the remaining pool of target gene polypeptide remains to provide function to the host cell. The second prong of the repression system is therefore specifically tied to removing this residual target gene polypeptide through a process of inducible targeted proteolysis.

4.3.3 N-end Rule Pathway Components and Corresponding Amino-Terminal Codons

The second prong of the two-pronged gene shut-off system is an inducible proteolytic means for the degradation of the existing pool of target gene polypeptide. In combination with the transcriptional shut-off described above, it provides for a thorough block to continued target gene function.

The targeted inducible proteolytic prong of the system makes use of an inducible promoter, as described above, to drive expression of a components of the so-called "N-end rule" system for proteolytic degradation (Bachmair et al. (1986) Science 234: 179–86). This system operates to degrade a cellular polypeptide at a rate dependent upon the amino-terminal amino acid residue of that polypeptide. Protein translation ordinarily initiates with an ATG methionine codon and so most polypeptides have an amino-terminal methionine residue and are typically relatively stable in vivo. For example, in the yeast *S. cerevisiae*, a beta-galactosidase polypeptide with a methionine amino terminus has a half-life of >20 hours (Varshavsky (1992) Cell 725–35). Under certain circumstances, however, polypeptides possessing a non-methionine amino-terminal residue can be created. For example, when an endoprotease hydrolyzes and thus cleaves a unique polypeptide bond (Y-X) internal to a polypeptide, it results in the release of two separate polypeptides—one of which possesses an amino-terminal amino acid, X, which may not be methionine. For example, the endoprotease ubiquitin isopeptidase, which is a preferred component of the present invention, will cleave a polypeptide bond carboxy-terminal to the final glycine residue (codon 76), regardless of what the next codon is. In the normal function of the cell, this isopeptidase serves to cleave a polyubiquitin precursor into individual ubiquitin units. However it can also be used to generate a target polypeptide with virtually any amino-terminal residue by merely fusing the target polypeptide in-frame to a codon corresponding to the desired amino-terminal amino acid (X), which codon, in turn, is fused downstream of ubiquitin (typically contiguous with ubiquitin Gly codon 76). The resulting target gene chimera construct, has the general structure Ubiquitin-X-Target. Preferred target constructs further comprise an epitope tag (Ep) so that the resulting target gene chimera construct has the general structure Ubiquitin-X-Ep-target, which results in the eventual production of a polypeptide of the general structure X-Ep-Target. Constitutively active ubiquitin isopeptidase activities present in eucaryotic cells will result in the endoproteolytic processing of the Ubiquitin-X-Target polypeptide into Ubiquitin and X-Target entities. The X-Target polypeptide is further acted upon by the components of the N-end rule system as described below.

It has been determined, with reasonable reliability, the relative effect of a given amino-terminal residue, X, upon target polypeptide stability. For example, when all 20 possible amino-terminal amino acid residues were tested to determine their effect on the stability of beta-galactosidase (utilizing a ubiquitin-X-beta-galactosidase chimeric fusion) in Saccharomyces cerevisiae, drastic differences were discovered (see Varshavsky (1992) Cell 69: 725–35). For example when X was met, cys, ala, ser, thr, gly, val, or pro, the resulting polypeptide was very stable (half-life of >20 hours). When X was tyr, ile, glu, or gln, the resulting polypeptide possessed moderate protein stability (half-life of 10–30 minutes). In contrast, the residues arg, lys phe, leu, trp, his, asp, and asn, all conferred low stability on the beta-galactosidase polypeptide (half-life of <3 minutes). The residue arginine (arg), when located at the amino terminus of a polypeptide, appears to generally confer the lowest stability. Thus, chimeric constructs and corresponding chimeric polypeptides employing an arg residue at the position X, described above, are generally preferred embodiments of the present invention. This is because a general goal of the invention is to eliminate the function of the target gene polypeptide in the cell.

The above described experiments establishing the relative half-lives conferred by each of the 20 possible amino terminal residues form the basis of the N-end rule. The N-end rule system components are those gene products which act to bring about the rapid proteolysis of polypeptides possessing amino-terminal residues which confer instability. The N-end rule system for proteolysis in eucaryotes appears to be a part of the general ubiquitin-dependent proteolytic system pathways possessed by apparently all eucaryotic cells. Briefly, this system involves the covalent tagging of a target polypeptide on one or more lysine residues by a ubiquitin polypeptide marker (to form a target(lys)-epsilon amino-gly(76)Ubiquitin covalent bond). Additional ubiquitin moieties may be subsequently conjugated to the target polypeptide and the resulting "ubiquitinated" target polypeptide is then subject to complete proteolytic destruction by a large (26S) multiprotein complex known as the proteasome. The enzymes which conjugate the ubiquitin moieties to the targeted protein include E2 and E3 (or ubiquitin ligase) functions. The E2 and E3 enzymes are thought to possess most of the specificity for ubiquitin dependent proteolytic processes.

Indeed a key component of the N-end rule proteolytic pathway in yeast is UBR1 (Bartel, et al. (1990) EMBO J. 9: 3179–89), a gene which encodes an E3 like function which appears to recognize polypeptides possessing susceptible amino terminal residues and thereby facilitates ubiquitination of such polypeptides (Dohmen et al. (1991) Proc. Natl. Acad. Sci. USA 88: 7351–55). In preferred embodiments of the invention, UBR1 is used as the N-end rule component which is the effector of proteolytic degradation of the target gene polypeptide. The UBR1 gene has now been cloned from a mammalian organism (Kwon et al. (1998) Proc. Natl. Acad. Sci. USA 95: 7893–903) as well as from yeast. Thus the construction of a UBR1 mouse knockout is imminent and so both prongs of the two-pronged gene function shut-off system can now be set up in both yeast and mammalian host cells.

A preferred embodiment of the N-end rule component of the two-component shut-off is the above described N-end rule ubiquitin ligase UBRI gene. This gene is particularly convenient since it can be used in conjunction with any of the above described "X" amino-terminal destabilizing residues including: the most destabilizing—arg; strongly destabilizing residues—such as lys phe, leu, trp, his, asp, and asn; and moderately destabilizing residues—such as tyr, ile, glu, or gln. Indeed, it is an object of the present invention to provide a means, where desired, to not completely shut-off a target gene's function, but merely to attenuate it to some set degree. This can be achieved using the method of the present invention in any of a number of ways. For example, a moderately destabilizing amino-terminal residue (X=tyr, ile, glu, or gin) can be deployed on the target polypeptide—resulting in a less rapid removal of the target polypeptide pool. Alternatively, only one of the two prongs of the method could be employed such as only the transcriptional repression prong or only the targeted proteolysis prong.

Alternative embodiments of the N-end rule component of the present invention include S. cerevisiae UBC2 ( RAD6), which encodes an E2 ubiquitin conjugating function which cooperates with the UBR1—encoded N-end rule E3 to promote multiubiquitination and subsequent degradation of N-end rule substrates (Dohmen et al. (1991) Proc. Natl. Acad. Sci. USA 88: 7351–55). Thus N-end rule directed proteolysis will not occur in the absence of either UBR1 or UBC2. This allows either gene to be used as the inducible "effector of targeted proteolysis" by the method of the present invention. Indeed, a target gene polypeptide possessing an N-end rule destabilizing amino-terminal amino acid (such as arg) will be stable until expression of either the UBR1 (E3) or the UBC2 (E2) is induced from the cognate inducible promoter construct.

Both UBR1 and UBC2 can be used in conjunction with any of the above described "X" amino-terminal destabilizing residues including: the most destabilizing—arg; strongly destabilizing residues—such as lys phe, leu, trp, his, asp, and asn; and moderately destabilizing residues—such as tyr, ile, glu, or gin. Still other alternative embodiments of the N-end rule component of the present invention are components of the N-end rule system which affect only a subset of the destabilizing residues. For example, the NTA1 deamidase (Baker and Varshavsky (1995) J Biol Chem 270: 12065–74) functions to deaminate amino-terminal asn or gin residues (to form polypeptides with asp or glu amino-terminal residues respectively). Yeast strains harboring nta1 null alleles are unable to degrade N-end rule substrates that bear amino-terminal asn or gin residues. Thus, the NTA1 gene is an alternative embodiment of the N-end rule component of the present invention, but is used preferably in conjunction with a target gene polypeptide (X-target), in which X is either asn or gin. Similarly the ATE1 transferase (Balzi et al. (1990) J. Biol Chem 265: 7464–71) is an enzyme which acts to transfer the arg moiety from a tRNA~Arg activated tRNA to amino-terminal glu or asp bearing polypeptides. The resulting arg-glu-polypeptide and arg-asp-polypeptide products are then susceptible to the E2/E3—mediated N-end rule dependent proteolytic processes described above. Thus, the ATE1 transferase is an alternative embodiment of the N-end rule component of the present invention, but its use is preferably tied to target gene polypeptides (X-target), in which X is asp, glu, asn or gln. Polypeptides bearing the latter two amino-terminal residues are first converted to polypeptides bearing one of the former tow amino-terminal residues by NTA1 deamidase function described above.

It is important to note here that, as is the case for the repressor of the present invention which is made subject to induction by an inducible promoter of the present invention, the N-end rule component must be available as a clone so that it can be put under the control of an inducible promoter (using standard subcloning methods known in the art). This can be achieved by first introducing a genetically engineered copies of the inducible repressor and the inducible N-end rule component constructs, and subsequently deleting the normal chromosomal copies of these genes from the host by "knockout" methods. Such methods, we note here are well developed in the art—particularly in the case of both the yeast *Saccharomyces cerevisiae* and the mammal mouse. More convenient, however, is the availability of "knock-in" technology which allows the existing chromosomal copy of the gene to be modified to so that its native promoter is deleted and an inducible promoter is inserted in a single step. FIG. 2A diagrams this process for the replacement of the native promoter of the target gene with a repressible promoter, but this principle is also applicable to the replacement of the native promoter of the effector of suppression (i.e. the transcriptional repressor and/or the N-end rule component) with a suitable inducible promoter.

4.3.4 Ubiquitin Polypeptide Sequences

As shown in FIG. 1B, the target gene must be fused downstream of a codon which encodes an N-end rule susceptible residue (X, as described above) and this residue, in term, must be fused in-frame to the carboxy-terminus of a ubiquitin coding sequence (generally gly76 of ubiquitin). The reason for constructing this extensive chimeric gene construct is to take advantage of the ability of constitutive ubiquitin proteases to cleave any peptide bond which is carboxy-terminal to gly76 of a ubiquitin moiety. This isopeptidase normally functions to process poly-ubiquitin chains (the translational product of the tandem ubiquitin encoding sequences of eucaryotic genomes) into discrete (normally 76 aa) ubiquitin moieties which are used in ubiquitin-system pathways. In the method of the present invention, the ubiquitin isopeptidases serve as a convenient means to generate target gene polypeptides bearing specific amino-terminal residues (X). Nonetheless, it is understood that other alternatives to mammalian or yeast ubiquitin exist which can function in the method of the present invention. Such ubiquitin equivalents include, for example, ubiquitin mutants, ubiquitin-like proteins, ubiquitin-related proteins, and ubiquitin-homologous proteins. For example, ubiquitin-like proteins such as NEDD8, UBL1, FUBI, and UCRP, as well as analogous ubiquitin-related proteins such as SUMO/Sentrin/Pic1 may be used as ubiquitin equivalents in the method of the invention. Other proteins related to ubiquitin, but which are somewhat less homologous to it, include ubiquitin-homologous proteins such as Rad23 and Dsk2 whose similarity to ubiquitin does not include the presence of a carboxyl-terminal pair of glycines. These ubiquitin-like proteins share the common features of being related to ubiquitin by amino acid sequence homology and, with the apparent exception of the ubiquitin homologous proteins, of being covalently transferred to cellular protein targets post-translationally.

Indeed, the intended scope of the immediate invention encompasses any means known in the art by which a target polypeptide bearing an N-end rule susceptible residue (X=arg, lys, his, leu, phe, tyr, ile, trp, asn, gln, asp, or glu) can be generated.

4.3.5 Target Genes

As discussed above, the method of the present invention is ideally suited to the analysis and exploitation of genes whose function is essential for viability. Moreover, the methods developed here allow virtually any gene to be made subject to either or both of the gene function shut-off prongs of the present invention. FIG. 2A diagrams the manner in which virtually any desired target gene comprising a native promoter (naPr) which drives expression of the target ORF (open reading frame) can be put under the control of a repressible promoter (rePr) which is subject to the transcriptional repression prong of the present invention. Furthermore, FIG. 2B diagrams the manner in which virtually any desired target gene target ORF can be fused in-frame with a Ubiquitin-X-Ep (in which Ep is an optional epitope tag which can be used to facilitate the measurement of target gene polypeptide levels) to create a gene sequence which encodes a target gene polypeptide which is subject to the targeted proteolytic destruction prong of the present invention. As noted earlier these construct can be created through either standard subcloning techniques known in the art, or by means of a "knock-in" construct which has the advantage of yielding the desired altered target gene in a single step. A detail description of the suitable mouse cell technology is provided below. FIG. 3 further diagrams how a single target gene can be made subject to control by both the transcriptional repression and the targeted proteolytic destruction prong of the invention.

Specific examples of preferred target genes include various components of the RNApolII transcriptional machinery, as described in the Example sections below. These include TAF60, TAF19, TAF90, TAF130, TFIIB, and TBP (see Moqtaderi et al. (1996) Nature 383: 188–91).

4.3.6 Other Methods

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a Target gene of interest in ES cells, these changes can be introduced into the germlines of animals to generate chimeras. The gene targeting procedure is accomplished by introducing into tissue culture cells a DNA targeting construct that includes a segment homologous to a target Target gene locus, and which also includes an intended sequence modification to the Target genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a Target gene function through the use of a targeting transgene construct designed to undergo homologous recombination with one or more Target genomic sequences. The targeting construct can be arranged so that, upon recombination with an element of a Target gene, a positive selection marker is inserted into (or replaces) coding sequences of the gene. The inserted sequence functionally disrupts the Target gene, while also providing a positive selection trait. Exemplary Target gene targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp.*

MoMFGFhol. 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene ($neo^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for Target gene or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targetted gene, resulting in a transgenic animal which expresses a polypeptide of the targetted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the MFGF gene knocked out in various tissues of the offspring by probing the Western blot with an antibody against the particular MFGF protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a Target-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A Target transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a Target gene protein can be essential for many forms of lineage analysis and can additionally provide a means to assess the effects of, for example, lack of Target gene expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject Target gene proteins. For example, excision of a target sequence which interferes with the expression of a recombinant Target gene, such as one which encodes an antagonistic homolog or an antisense transcript, can be designed to activate expression of that gene. This interference with expression of the protein can result from a variety of mechanisms, such as spatial separation of the Target gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant Target gene protein can be regulated via control of recombinase expression.

Use of the cre/loxP recombinase system to regulate expression of a recombinant Target gene protein requires the construction of a transgenic animal containing transgenes encoding both the Cre recombinase and the subject protein. Animals containing both the Cre recombinase and a recombinant Target gene can be provided through the construction of "double" transgenic animals. A convenient method for providing such animals is to mate two transgenic animals each containing a transgene, e.g., a Target gene and recombinase gene.

One advantage derived from initially constructing transgenic animals containing a Target transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic Target transgene is silent will allow the study of progeny from that founder in which disruption of Target gene mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the Target transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a Target A transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-$2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred.

It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a Target protein (either agonistic or antagonistic), and antisense transcript, or a Target mutant.

Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

5. Examples

The present invention is further illustrated by the following examples which should not be construed as limiting in any way. The contents of all cited references (including literature references, issued patents, published patent applications as cited throughout this application are hereby expressly incorporated by reference.

The practice of the present invention will employ, unless otherwise indicated, conventional techniques of cell biology, cell culture, molecular biology, microbiology and recombinant DNA, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); B. Perbal, A Practical Guide To Molecular Cloning (1984); the treatise, Methods In Enzymology (Academic Press, Inc., N.Y.); Methods In Enzymology, Vols. 154 and 155 (Wu et al. eds.), Immunochemical Methods In Cell And Molecular Biology (Mayer and Walker, eds., Academic Press, London, 1987).

5.1 Example 1

Use of Double Shutoff Yeast Strain Containing Copper-Inducible Yeast Alleles of Both ROX1 And UBR1 to Determine that TBP-Associated Factors are not Generally Required for Transcriptional Activation in Yeast Materials and Methods The parent strain ZMY60, containing copper-inducible alleles of UBR1 and ROX1, was created as follows. A cassette containing the copper-inducible derivative of the HIS3 promoter (Klein, C and K. Struhl (1994) *Science* 266: pp. 280–282) and 2 kb of upstream flanking sequence was inserted at the initial ATG of a plasmid-borne genomic fragment of ROX1 to create the URA3 integrating plasmid ZM195. The same cassette was inserted at the initial ATG of UBR1 to create ZM197. Both of these copper-driven alleles were introduced into yeast strain KY114 (Iyer, V and K. Struhl (1995) *Mol. Cell. Biol.* 116: pp. 7069–7086) in successive two-step gene replacements. To create TAF disruption molecules, another cassette comprising an inframe fusion of ubiquitin, arginine, Lac1 and the HA epitope driven by the ANB1 promoter, was fused in-frame to a short 5' fragment of TAF coding sequence beginning at the initial TAF ATG. To create a given conditional knockout strain, the relevant TAF knockout molecule on a URA3 integrating plasmid was linearized within the TAF coding sequence fragment and transformed into ZMY60. This integration results in homologous recombination at the TAF locus to yield a short, non-functional 5' TAF piece under its normal promoter, followed immediately downstream by a full-length copy of the tagged TAF under the ANB1 promoter. Selection for uracil prototrophy was maintained in all experiments to avoid loss of the integrated plasmid.

RNA levels were determined by the quantitative S1 analysis as described (Cormack, B. P. et. al., (1994) *Genes Dev.* 8: pp. 1335–1343; Iyer, V., and K. Struhl (1996) *Proc. Natl. Acad. Sci. USA* 98: pp. 5208–5212). All hybridization reactions contained at least two probes, such that the relative levels of all transcripts were internally controlled. The error for any particular RNA determination is ±30%. TAF levels were determined by western blotting, with bands being detected by chemiluminescence (ECL). Relative levels of TAFs at various times were determined by comparing band intensities to serially diluted samples from wild-type cells.

Results

As described above, a two-pronged approach was used to create strains with conditional TAF alleles in which the addition of copper ion leads to the simultaneous cessation of TAF messenger RNA synthesis and destruction of any TAF protein present in the cell. Strains with conditional alleles of TAF130 (TAF145), TAF90, TAF60 and TAF19 (Fun81), which are homologous to human TAF250, Drosophila TAF80, Drosophila TAF60 and human TAF18, respectively, were generated. Of these, TAF130 is particularly interesting, as it appears to be the scaffold on which the remaining TAFs assemble into the TFIID complex (Chen, J.-L., et. al., (1994) *Cell* 79: pp. 93–105) As controls, strains containing conditional alleles of TFIIB and TBP were generated. In all cases, the conditional knockout strains fail to grow on copper-containing medium, and the addition of copper ion caused cells to stop growing within about six hours. TAF90-depleted cells arrest frequently as large, budding cells, whereas cells depleted of other TAFs display variable and abnormal morphologies.

In general, transcription was analysed 8 hours after copper ion addition, when more than 95% of the cells were dead (they were unable to grow when returned to medium lacking copper). At this time, western blotting reveals that levels of TAF130, TAF90 and TBP are less than 5% of wild type. Although TAFs may not be completely eliminated by this procedure, they are reduced to less than 100–200 molecules per cell (Walker, S. S., et. al., (1996) *Nature* 385: pp. 185–188), which is considerably less than the number of Pol II promoters per cell (~6,000).

When cells are grown under standard conditions, TAF depletion affects transcription of selected Pol II promoters. Depletion of TAF130, TAF60, TAF90 and TAF19 does not significantly affect transcription of ded1 or his3+13, promoters with canonical TATA elements (Chen, W. and K. Struhl (1985) *EMBO J.*, 4: pp. 3272–3280; Iyer, V. and K. Struhl (1995) *Mol. Cell. Biol.*, 15: pp. 7059–7066). However, depletion of TAF130 significantly reduces the level of the trp3 and his3+1 transcripts, which arise from promoters with suboptimal, nonconsensus TATA elements (Iyer, V. and K. Struhl (1995) *Mol. Cell. Biol.* 15: pp. 7059–7066; Martens, J. A. and Brandt, C. J. (1994) *J. Biol. Chem.*, 269: pp. 15661–15667). This preferential effect on transcription from promoters containing weak TATA elements is also observed when TAF19 is depleted, albeit to a lesser extent and with slower kinetics, but it does not occur upon depletion of TAF90 or TAF60. Interestingly, the transcriptional pattern resulting from TAF130 or TAF19 depletion is similar to that mediated in yeast by human TBP, which has been suggested to interact inefficiently with yeast TAFs (Cormack, B. P., et. al. (1994) *Genes. Dev.* 8: pp. 1335–1343). As expected, depletion of TBP or TFIIB results in a rapid and large reduction of all mRNA species tested. At a late time point (11 hours), depletion of TAF90 confers a moderate decrease of all transcripts. It is unclear whether this effect reflects a specific function of TAF90 or arises indirectly from cell death.

Surprisingly, when the conditional knockout strains are grown under conditions that support activation by Gcn4 or Ace1, TAF depletion does not significantly affect the level of activated transcription (Ace1-dependent activation appears slightly reduced upon TAF90 depletion). In contrast, depletion of TFIIB causes the loss of activated transcription in both situations. The observed Gcn4- and Ace1-activated transcription reflects initiation events that occur under conditions of TAF depletion, because mRNA half-lives are very short in comparison to the timescale of the experiment.

One explanation for the maintenance of Gcn4 and Ace1 activation after TAF depletion is that TAFs present in active transcription complexes might be preferentially sequestered from Ubr1-dependent degradation. To examine whether active transcription complexes could be assembled after TAF depletion, the conditional knockout strains were grown in non-inducing conditions, treated with copper for 8 hours, and then tested for the ability to mediate activator-dependent transcription de novo. All the TAF-depleted strains show significant activation by Gal4 and heat-shock factor upon exposure to the relevant inducer, whereas activation is not observed in the TFIIB-depleted strain. Similarly, efficient Ace1-dependent activation was observed after TAFs were depleted either by placing the TAF genes under the control of the GAL1, 10 promoter and shifting cells to glucose or by shifting a tsm1 (dTAF150 homologue) strain to the restrictive temperature. The heat-shock and Ace1 activation responses in the TAF-depleted strains are comparable to the parental strain; Gal4 activation is reduced 3–4 fold. However, as very small fluctuations in Gal4 levels or changes in growth potential can have pronounced effects on Gal4-dependent transcription (Griggs, D. W. and M. Johnston (1991) *Proc. Natl. Acad. Sci. USA,* 88 pp. 8597–8601), it is unclear whether the decrease reflects a mild activation defect or whether Gal4 expression is slightly perturbed for other reasons. Previously described activation-defective yeast strains are considerably more impaired for Gal4-dependent activation, and they are defective in the response to other acidic activators (Arndt, K. M. et. al., (1995) *EMBO J.,* 14: pp. 1490–1497; Lee, M. and K. Struhl (1995) *Mol. Cell. Biol.* 15: 5461–5469; Stargell, L. A. and Struhl, K. (1995) *Science,* 269: pp. 75–78).

Since TAF depletion does not significantly affect activation by Gcn4, Ace1, Gal4, Hsf, and unidentified activators involved in ded1 and his3+13 transcription, TAFs do not appear to be required for transcriptional activation in yeast cells. This conclusion was reached independently in experiments where TAF depletion was obtained using temperature-sensitive mutants or a glucose shutoff procedure (Hernandez, N. (1993) *Genes Dev.,* 7: pp. 1291–1308). It is particularly striking that this is true of TAF130, which provides the scaffold for TAF assembly and without which TFIID is likely to be disrupted. Although TAFs are not generally required for transcriptional activation, they are essential for cell growth. One possibility is that TAFs are required for the response to a subset of activators that affect one or more essential genes. Alternatively, TAFs could subtly affect activation of many genes, such that the cumulative effects lead to cell inviability. Finally, as suggested by the effects on trp3 and his3+1 transcription, TAFs may be important for transcription from promoters with weak TATA elements.

This conclusion is in apparent contrast to numerous experiments in vitro, which indicate that TAFs are crucial in all activated transcription. This probably does not indicate that yeast TAFs are less important than their mammalian and Drosophila counterparts because: (a) TAFs are strongly conserved among eukaryotes; (2) TAF-dependent activation in vitro can be achieved with yeast components (Reese, J. et. al. (1994) *Nature,* 371: 523–527; Poon, D. et. al. (1995) *Proc. Natl. Acad. Sci. USA,* 92: 8224–8228); and (3) activation can occur in a hamster cell line in which TAF250 (yeast TAF130 homologue) has been thermally inactivated (Fos transcription occurs normally, and it is unclear whether the reduction of cyclin A transcription is an indirect effect of cell-cycle arrest or a direct effect of TAF250) (Wang, E. H. and Tijian, R., (1994) *Science,* 263: pp. 811–814). A more likely explanation is that TAFs are functionally redundant with other factors that are absent in typical in vitro reactions. Indeed, activated transcription in the apparent absence of TAFs can occur in vitro when reactions either contain Pol II holoenzyme (Koleske, A. J. and Young, R. A. (1994) *Nature,* 368: pp. 446–469; Kim, Y.-J. et. al., (1994), *Cell,* 77: 599–608) or are performed on chromatin templates (Balasubramanian, B., et. al., (1993) *Mol. Cell. Biol.* 13: pp. 6071–6078). Moreover, most in vitro transcription reactions are reconstituted with core Pol II, and hence may lack components of the Pol II holoenzyme (for example, Srb proteins, Gal 11) that are functionally important in vivo (Koleske, A. J. and Young, R. A. (1995) *Trends Biochem. Sci.,* 20: pp. 113–116).

A common view of the transcriptional activation process is that activator proteins stabilize the Pol II machinery at the promoter, thereby permitting increased transcriptional initiation (Struhl, K. (1996) *Cell,* 84: pp. 179–182). In principle, activator proteins can interact with individual components of the Pol II machinery, and indeed, artificial connection of enhancer-bound proteins to TBP (Chatterjee, S. and Struhl, K., (1995) *Nature,* 374: pp. 820–822; Klages, N. and Strubin, M., (1995), *Nature*, 374: 822–823), TAFs and components of the Pol II holoenzyne (Barberis, A. et. al. (1995) *Cell*, 81: 359–368) can bypass the need for an activation domain. If natural activators interact with multiple components, individual components such as TAFs are likely to be non-essential for activation, even if they are potential targets. Thus, although it is possible to generate conditions in which TAFs are required for activation in vitro, they do not appear to be generally required in vivo. However, at promoters lacking conventional TATA elements, which are inherently weak targets for TFIID, interactions of TAFs with basic transcription factors or with promoter DNA may be important for stabilizing the Pol II machinery.

5.2 Example 2

The following example demonstrates how any given target gene can be configured for the double shutoff system in *Saccharomyces cervisiae*. The system requires two basic components: first, a parent strain containing copper-inducible alleles of both ROX1 and UBR1; and second, a short 5' fragment of the target gene of interest fused in frame to a ubiquitin-arginine-lacI-HA ("URLF") cassette and driven by the ANB1 promoter.

The strain ZMY60 has the genotype: MAT ay, ACE-UBR1, Ace-ROX1, trpl-D1, ura3-52Z LEU2, HIS3, ade2-101 in a KY114 background. To generate a parent strain in a different background, one utilizes the URA3 integrating plasmids ZM195 and AM197, which must be used in successive two-step gene replacements to generate a parent strain containing copper-inducible ROX1 and UBR1. To create double-shutoff parent strain, one integrates ZM195 into a desired strain with AflII. The URA3 marker is the loopout on FOA (5-fluorotica acid). One would then check for correct loopouts by Southern blotting analysis. Next, one transforms a correctly ROXl-replaced strain with AatII-digested AM197 and one loopout on FOA. Check by Southern.

{Southern details: With the ZM195 integration, digest with PvuII, and probe with a 5' piece of the ROX1 ORF (for example, the 550 bp cla1-Pst1 fragment of ZM195). Correct loopouts will pick up a band at about 3 kb, wildtype ROX1 at about 1 kb.

With ZM197, digest with Stu1 and Bgl2, and probe with a 5' piece of the UBR1 ORF (e.g., the 550 bp Hind3 fragment of ZM197). Correct loopouts will again be 2 kb larger than incorrect ones.}

To create the ANB-URLF gene fusion, digest or PCR out a short, nonfunctional (usually about 300 bp) fragment the gene beginning at the initial ATG. The fragment should contain a convenient unique restriction site (not too close to either end, and preferably closer to the 3' end of your fragment than to the fusion junction) to allow for efficient integration of the final plasmid at the normal gene locus. Using the reading frame information provided, clone the fragment in frame into ZM168, and then transfer the resulting ANB-URLF-gene fragment into a desired yeast integrating vector. Alternatively, both steps can be done at once with a 3-piece ligation.

To use the system:
1. Digest the ANB-URLF-gene construct with the internal restriction enzyme, and transform the resulting product into ZMY60 or the parent strain. Plate the transformants onto synthetic complete plates lacking the plasmid marker.
2. Test the transformants on plates lacking or containing 500 μM copper sulfate. Be sure to maintain selection for the marker so as not to allow looping out of the integrated plasmid. If the gene is essential, the cells should fail to grow in the presence of copper. More or less copper may be used depending on the level of shutoff seen with the particular gene, but in general, 500 μM is effective.

5.3 Example 3

DKO strains and constructs of TAF19 (strain ZMY67), TAF60 (ZMY66), TAF90 (ZMY68), TAF 130 (ZMY69, TBP, AND TFIIB (ZMY71).

Strain ZMY60 (the DKO parent strain)
Useful *Saccharomyces cervisiae* Strains
Parent Strains
  ZMY59 (Ace-UBR1 only strain)
  ZMY61 (Ace-ROX1 only strain)
  ZMY103 (ZMY60 his3Δ200)
  ZMY117 (ZMY60 leu2::PET56)
  ZMY118 (ZMY60 his3Δ200, leu2::PET56)
Shutoff Strains
  ZMY65 (TSM1 DKO)
  ZMY70 (HIS3 DKO)
  ZMY75 (triple-HA-tagged TAF130 DKO)
  ZMY76 (has complete gene replacement of TAF130 for ANB-URLF-TAF130)
  ZMY119 (TOA1 DKO strain)
  ZMY95 (triple-HA-tagged TAF23 DKO)
  ZMY96 (triple-HA-tagged TAF40 DKO)
  ZMY97 (triple-HA-tagged TAF67 KO)
  ZMY131 (TAF17 DKO)
  ZMY133 (triple-HA-tagged TAF60 KO)
  ZMY134 (TAF60 DKO-complete gene replacement)
Strains with Single-prong Shutoffs
  ZMY62 (TSM1 Ub only)
  ZMY63 (TAF90 ub only)
  ZMY64 (AF130 ub only)
  HIS3 rox-only KO strain The TAFs were shut-off by expressing each under direct control of the GAL 1,10 UAS+switching to glucose and by using the Ace-HIS3 (Klein and Struhl) promoter, growing in the presence of copper and then shifting by removing the copper (this, however, is less efficient than with galactose—cell growth never actually stopped, only slowed.)

The ub-only prong was tested by using a reporter plasmid (obtained from Dan Finley) called pUB23L (incorporating a Leu as the N-end residue in front of a ub-b-gal reporter. In the presence of 200 μM copper and X-gal, the ub-only strain ZMY59 with this reporter is white. Without copper, it is blue.

A HIS3 DKO and a HIS3 Rox-only strain was tested and found that in the presence of 500 μM CuS04, both failed to grow on plates lacking histidine. Without copper, growth was entirely normal on plates lacking histidine.

The urlf allele is usually introduced by means of a one-step integration that simultaneously truncates the endogenous copy. (This could also be done by shuffling in a cen plasmid in a null strain). The strain ZMY76 can stably integrate the urlf allele with a 2-step gene replacement. This means that there is no truncated piece left upstream, and no remaining repeated sequence fragments requiring maintenance of selection for the integrating plasmid marker.

Testing the system: Growth of the indicated strains (+=strong growth; −=no growth; +/−=intermediate growth; ND=not determined).

| Allele | 100 μMCu | 250 μMCu | 500 μMCu | 1 mM |
|---|---|---|---|---|
| ub-only TAF90 | + | ND | − | ND |
| DKO TAF90 | +/− | − | − | − |
| ub-only TAF130 | + | + | + | ND |
| DKO TAF130 | +/− | − | − | − |
| DKO TFIIB | ND | − | − | − |
| ub-only TSM1 | + | + | + | + |
| DKO TSM1 | + | + | +/− | − |

Lee and Lis (1998) have used the system to shut off SRB4 and KIN28 (Nature 393:389–92)

I have used the system to shut off TOA1 (loss of much PolII tx-manuscript in prep), TAFs17, 40 and 67 (submitted—17 causes a general loss of tx, and 40 and 67 cause gene-specific defects), and TAF23.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A method for inducibly repressing the transcription of a target gene expressed from a repressible promoter in a eukaryotic cell comprising:
   providing a eukaryotic cell comprising a target gene expressed from a repressible promoter and
   a nucleic acid encoding a transcriptional repressor expressed from an inducible promoter, which transcriptional repressor represses said repressible promoter, and
   contacting the cell with an inducing agent that induces said inducible promoter in order to express said transcriptional repressor and repress said repressible promoter, thereby causing the transcriptional repression of said target gene in the eukaryotic cell.

2. The method of claim 1, wherein the inducible promoter is repressed by a derepressible repressor and wherein said derepressible repressor is further subject to targeted proteolysis by the N-end rule system.

3. The method of claim 1, wherein the eukaryotic cell is a yeast cell.

4. The method of claim 3, wherein the yeast is *Saccharomyces cerevisae*.

5. A method for inducibly repressing the transcription of a target gene expressed from a repressible promoter, wherein the target gene encodes a chimeric polypeptide comprising ubiquitin and a target polypeptide comprising:
   providing a target gene operably linked to a repressible promoter, wherein the target gene encodes a chimeric polypeptide comprising ubiquitin and a target polypeptide, wherein said ubiquitin permits rapid removal of said chimeric polypeptide,
   providing a gene encoding a transcriptional repressor operably linked to an inducible promoter, which transcriptional repressor represses the repressible promoter, and
   providing an inducing agent that induces said inducible promoter in order to express said transcriptional repressor and repress said repressible promoter,
   thereby causing the transcriptional repression of said target gene.

6. The method of claim 5, wherein the target gene and the gene encoding the transcriptional repressor are in a eukaryotic cell.

7. The method of claim 6, wherein the eukaryotic cell is a yeast cell.

8. The method of claim 7, wherein the yeast is *Saccharomyces cerevisae*.

9. The method of claim 7, wherein the repressible promoter is a promoter from a gene selected from the group consisting of ANB1, HEM 13, ERG 11, OLE 1, GAL1, GAL10, and TET$^R$.

10. The method of claim 7, wherein the transcriptional repressor is selected from the group consisting of ROX1, Tet repressor, and lacI repressor.

11. The method of claim 7, wherein the inducible promoter is a copper—inducible promoter.

12. The method of claim 7, wherein the inducible promoter is inducible by $Cu^{+2}$, tetracycline, or an inducer of the lac operon.

13. A method for inducibly degrading a target polypeptide in a cell comprising:
   providing a cell comprising:
      a ubiquitin-target polypeptide fusion protein in which a specific amino terminal amino acid residue of said target polypeptide is contiguously joined by a peptide bond to a carboxyl terminal residue of a ubiquitin polypeptide;
      a ubiquitin isopeptidase which endoproteolytically cleaves said peptide bond thereby liberating said specific amino terminal amino acid residue of said target polypeptide from said carboxyl terminal residue of said ubiquitin polypeptide;
      an inducible component of the N-end rule system for ubiquitin dependent proteolytic destruction of said target polypeptide possessing said liberated amino terminal amino acid residue, and
   inducing said inducible component of the N-end rule system,
   thereby causing the inducible degradation of said target polypeptide possessing said liberated amino terminal amino acid residue in the cell.

14. The method of claim 13, wherein the cell is a eukaryotic cell.

15. The method of claim 14, wherein the eukaryotic cell is a yeast cell.

16. The method of claim 15, wherein the yeast is *Saccharomyces cerevisae*.

17. The method of claim 15, wherein the target polypeptide is a TBP-Associated Factor (TAF).

18. The method of claim 15, wherein the specific amino terminal amino acid residue of said target polypeptide is arginine.

19. The method of claim 15, wherein the specific amino terminal amino acid residue of said target polypeptide is selected from the group consisting of arginine, lysine and histidine.

20. The method of claim 15, wherein the specific amino terminal amino acid residue of said target polypeptide is selected from the group consisting of phenylalanine, tryptophan, tyrosine, leucine, and isoleucine.

21. The method of claim 15, wherein the specific amino terminal amino acid residue of said target polypeptide is selected from the group consisting of aspartate, glutamate, cysteine, asparagine and glutamine.

22. The method of claim 15, wherein said inducible component of the N-end rule system is an inducible transgene encoding a component of the N-end rule system for ubiquitin dependent proteolytic destruction.

23. The method of claim 15, wherein said component of the N-end rule system is selected from the group consisting of UBR1, UBC2, NTA1, and ATE1.

24. The method of claim 15, wherein said component of the N-end rule system is selected from the group consisting of mouse UBR1p and human UBR1p.

25. The method of claim 15, wherein the target polypeptide is a component of the RNA polII transcriptional machinery.

26. The method of claim 21, wherein the inducible component of the N-end rule system of the target polypeptide is an inducible transgene encoding an ATE1 transferase.

27. The method of claim 21, wherein the specific amino terminal amino acid residue of said target polypeptide is glutamine or asparagine and the inducible component of the N-end rule system of the target polypeptide is an inducible transgene encoding a deamidase specific for an amino-terminal glutamine or asparagine.

28. A method for repressing the function of a target gene expressing a target polypeptide in a cell by repressing the transcription of said target gene and degrading said target polypeptide, said method comprising:

inducibly repressing the transcription of said target gene by the method of claim 5, and inducibly degrading said target polypeptide by the method of claim 13, thereby repressing the function of said target gene by causing the inducible repression of said target gene and causing the inducible degradation of said target polypeptide in the cell.

29. The method of claim 28, wherein the cell is a eukaryotic cell.

30. The method of claim 29, wherein the eukaryotic cell is a yeast cell.

31. The method of claim 30, wherein the yeast is *Saccharomyces cerevisae*.

32. A method for repressing the function of a target gene expressing a target polypeptide in a cell by repressing the transcription of said target gene and degrading said target polypeptide, said method comprising:

inducibly repressing the transcription of said target gene, and inducibly degrading said target polypeptide by the method of claim 13 thereby repressing the function of said target gene by causing the inducible repression of said target gene and causing the inducible degradation of said target polypeptide in the cell.

33. The method of claim 32, wherein the cell is a eukaryotic cell.

34. The method of claim 33, wherein the eukaryotic cell is a yeast cell.

35. The method of claim 34, wherein the yeast is *Saccharomyces cerevisae*.

36. A method for repressing the function of a target gene expressing a target polypeptide by repressing the transcription of said target gene and degrading said target polypeptide in a cell, said method comprising:

inducibly repressing the transcription of said target gene, and inducibly degrading said target polypeptide thereby repressing the function of said target gene by causing the inducible repression of said target gene and causing the inducible degradation of said target polypeptide in the cell.

37. The method of claim 36, wherein the cell is a eukaryotic cell.

38. The method of claim 37, wherein the eukaryotic cell is a yeast cell.

39. The method of claim 38, wherein the yeast is *Saccharomyces cerevisae*.

40. A eukaryotic cell comprising:

a target gene encoding a target polypeptide, and an inducible transgene encoding a component of the N-end rule system for ubiquitin dependent proteolytic destruction for the degradation of said target polypeptide encoded by said target gene.

41. The eukaryotic cell of claim 40, which is a yeast cell.

42. The eukaryotic cell of claim 41, wherein the yeast is *Saccharomyces cerevisae*.

43. The eukaryotic cell of claim 41, wherein said component of the N-end rule proteolytic system is selected from the group consisting of UBR1, UBC2 and NTA1.

44. The eukaryotic cell of claim 41, in which said target gene is expressed from a repressible promoter.

45. The eukaryotic cell of claim 44, further comprising an inducible transcriptional repressor, which transcriptional repressor represses said repressible promoter.

46. The eukaryotic cell of claim 45, wherein said repressible promoter is a promoter from a gene selected from the group consisting of ANB1, HEM 13, ERG 11, OLE 1, GAL1, GAL10, and TET$^R$.

47. The eukaryotic cell of claim 45, wherein said transcriptional repressor is selected from the group consisting of ROX1, Tet repressor, and lacI repressor.

* * * * *